US00PP33833P2

(12) United States Plant Patent
Lommerse et al.

(10) Patent No.: US PP33,833 P2
(45) Date of Patent: Jan. 4, 2022

(54) ***PERSICARIA* PLANT NAMED 'FLAMINGO FEATHERS'**

(50) Latin Name: *Persicaria amplexicaulis*
Varietal Denomination: Flamingo Feathers

(71) Applicant: FUTURE PLANTS LICENTIE B.V., Lisserbroek (NL)

(72) Inventors: Gerardus Adrianus Petronella Lommerse, Noordwijkerhout (NL); Hendrikus Petrus Lommerse, Lisse (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 17/190,875

(22) Filed: Mar. 3, 2021

(51) Int. Cl.
*A01H 5/02* (2018.01)

(52) U.S. Cl.
USPC ..... Plt./467

(58) Field of Classification Search
USPC ..... Plt./467
See application file for complete search history.

*Primary Examiner* — Annette H Para
(74) *Attorney, Agent, or Firm* — C. Anne Whealy

(57) ABSTRACT

A new and distinct cultivar of *Persicaria* plant named 'Flamingo Feathers', characterized by its upright to broadly spreading plant habit; vigorous growth habit and moderate to rapid growth rate; durable and healthy medium green-colored leaves; early and freely flowering habit; long flowering period; long straight and slender inflorescences with numerous flowers that are bright pink in color; and good garden performance.

2 Drawing Sheets

Figure 1:
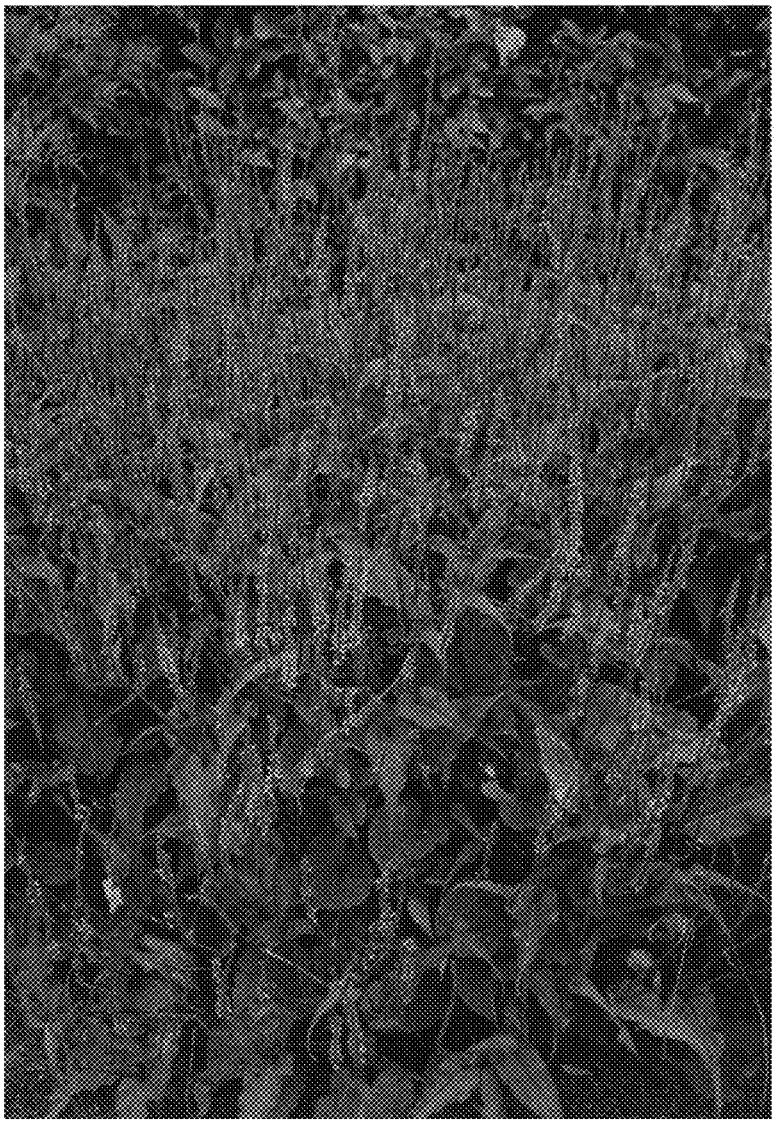

Botanical designation: *Persicaria amplexicaulis.*
Cultivar denomination: 'FLAMINGO FEATHERS'.

STATEMENT REGARDING PRIOR DISCLOSURES BY INVENTOR & APPLICANT/ASSIGNEE

The Inventors and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventors and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Persicaria* plant, botanically known as *Persicaria amplexicaulis*, also known as *Bistorta amplexicaulis* and hereinafter referred to by the name 'Flamingo Feathers'.

The new *Persicaria* plant is a product of a planned breeding program conducted by the Inventors in Lisserbroek, The Netherlands. The objective of the breeding program is to create new and unique *Persicaria* plants.

The new *Persicaria* plant originated from an open-pollination during the late summer of 2016 of *Persicaria amplexicaulis* 'Rosea', not patented, as the female, or seed, parent with an unknown proprietary selection of *Persicaria amplexicaulis* as the male, or pollen, parent. The new *Persicaria* plant was discovered and selected by the Inventors as a single flowering plant from within the progeny of the stated open-pollination in a controlled environment in Lisserbroek, The Netherlands during the summer of 2017.

Asexual reproduction of the new cultivar by divisions in Lisserbroek, The Netherlands since the winter of 2017 has shown that the unique features of this new *Persicaria* plant are stable and reproduced true to type in successive generations.

SUMMARY OF THE INVENTION

Plants of the new *Persicaria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Flamingo Feathers'. These characteristics in combination distinguish 'Flamingo Feathers' as a new and distinct *Persicaria* plant:

1. Upright to broadly spreading plant habit.
2. Vigorous growth habit and moderate to rapid growth rate.
3. Durable and healthy medium green-colored leaves.
4. Early and freely flowering habit; long flowering period.
5. Long straight and slender inflorescences with numerous flowers that are bright pink in color.
6. Good garden performance.

Plants of the new *Persicaria* can be compared to plants of the female parent, 'Rosea'. Plants of the new *Persicaria* differ primarily from plants of 'Rosea' in the following characteristics:

1. Plants of the new *Persicaria* are shorter than plants of 'Rosea'.
2. Leaves of plants of the new *Persicaria* are more durable and healthier than leaves of plants of 'Rosea'.

3. Flowers of plants of the new *Persicaria* are darker pink in color than flowers of plants of 'Rosea'.

Plants of the new *Persicaria* can be compared to plants of *Persicaria amplexicaulis* 'Pink Elephant', not patented. In side-by-side comparisons, plants of the new *Persicaria* differ primarily from plants of 'Pink Elephant' in the following characteristics:

1. Plants of the new *Persicaria* are taller than plants of 'Pink Elephant'.
2. Leaves of plants of the new *Persicaria* are more durable and healthier than leaves of plants of 'Pink Elephant'.
3. Flowers of plants of the new *Persicaria* are darker pink in color than flowers of plants of 'Pink Elephant'.
4. Inflorescences of plants of the new *Persicaria* are straight whereas inflorescences of plants of 'Pink Elephant' are undulating.

Plants of the new *Persicaria* can also be compared to plants of *Persicaria amplexicaulis* 'Summer Dance', not patented. In side-by-side comparisons, plants of the new *Persicaria* differ primarily from plants of 'Summer Dance' in the following characteristics:

1. Plants of the new *Persicaria* have a finer (less coarse) texture than plants of 'Summer Dance'.
2. Plants of the new *Persicaria* flower earlier than plants of 'Summer Dance'.
3. Flowers of plants of the new *Persicaria* are slightly darker pink in color than flowers of plants of 'Summer Dance'.

BRIEF DESCRIPTION OF THE PHOTOGRAPHS

The accompanying colored photographs illustrate the overall appearance of the new *Persicaria* plant showing the colors as true as it is reasonably possible to obtain in colored reproductions of this type. Colors in the photographs may differ slightly from the color values cited in the detailed botanical description which accurately describe the actual colors of the new *Persicaria* plant.

The photograph on the first sheet (FIG. 1) is a side perspective view of typical flowering plants of 'Flamingo Feathers' grown in an outdoor nursery.

Figure 2:
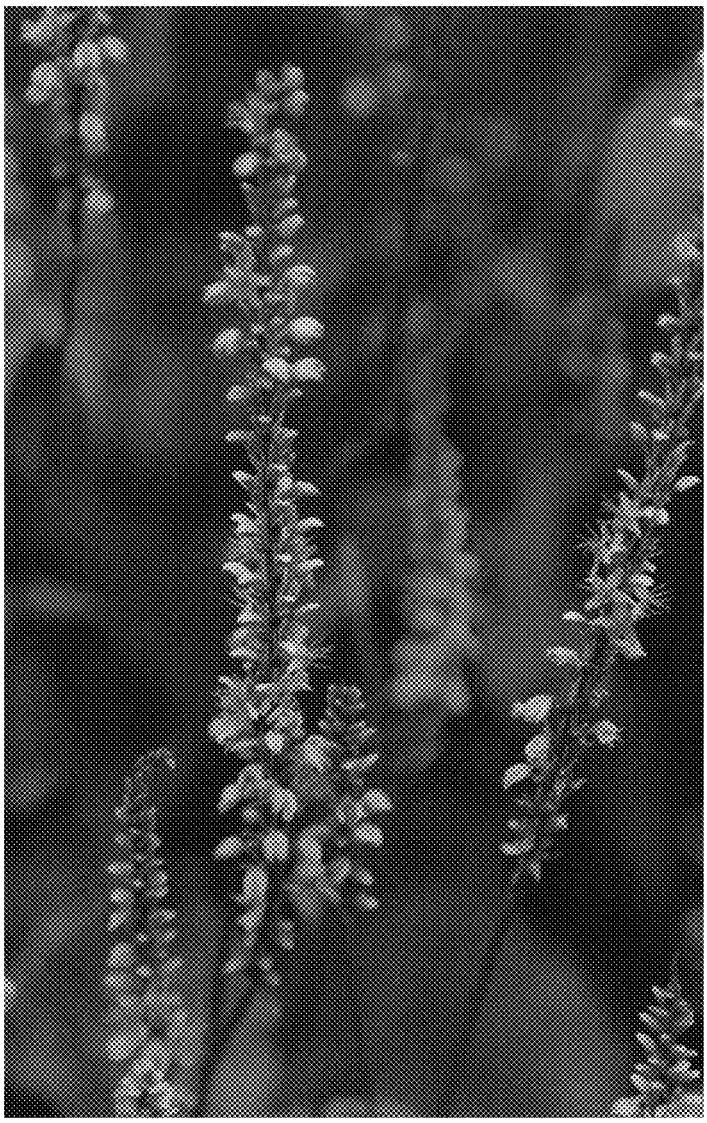

The photograph on the second sheet (FIG. 2) is a close-up view of typical inflorescences of 'Flamingo Feathers'.

DETAILED BOTANICAL DESCRIPTION

The aforementioned photographs and following observations and measurements describe plants grown during the late summer in ground beds in an outdoor nursery in Lisserbroek, The Netherlands and under conditions and cultural practices which approximate those typically used in commercial *Persicaria* plant production. During the production of the plants, day temperatures ranged from 13° C. to 30° C. and night temperatures ranged from 8° C. to 18° C. Plants were three years old when the photographs and description were taken. In the following description, color references are made to The Royal Horticultural Society Colour Chart, Sixth Edition, 2015, except where general terms of ordinary dictionary significance are used. Measurements represent averages for typical flowering plants.

Botanical classification: *Persicaria amplexicaulis* 'Flamingo Feathers'.

Parentage:

*Female, or seed, parent.*—*Persicaria amplexicaulis* 'Rosea', not patented.

*Male, or pollen, parent.*—Unknown proprietary selection of *Persicaria amplexicaulis*, not patented.

Propagation:

*Type.*—By divisions.

*Time to produce a rooted young plant.*—About 13 weeks at temperatures ranging from about 5° C. to 20° C.

*Root description.*—Medium to fine in thickness, slightly fibrous; typically greyed white in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Herbaceous perennial typically grown as a container and garden plant; upright to broadly spreading plant habit; overall plant shape is broadly oblong to globular; vigorous growth habit and moderate to rapid growth rate.

*Branching habit.*—Freely branching habit with about 34 primary lateral branches and about 80 secondary lateral branches developing per plant; pinching is not required.

*Plant height, soil level to top of foliar plane.*—About 83 cm.

*Plant height, soil level to top of floral plane.*—About 120 cm.

*Plant width.*—About 95 cm.

*Primary branch description.*—Length (excluding inflorescence): About 28.6 cm. Diameter: About 5 mm. Internode length: About 16.9 cm. Shape: Rounded. Strength: Strong. Aspect: About 10° to 20° from vertical. Texture and luster: Smooth, glabrous; moderately glossy. Color, developing: Close to 146C. Color, developed: Close to 146C; on sun-exposed surfaces, moderately to strongly tinged with close to 178A.

Leaf description:

*Arrangement.*—Alternate; simple.

*Length, basal leaves.*—About 19 cm.

*Width, basal leaves.*—About 10.5 cm.

*Length, cauline leaves.*—About 16.5 cm.

*Width, cauline leaves.*—About 6.4 cm.

*Shape, basal and cauline leaves.*—Ovate to narrowly ovate; slightly carinate.

*Apex, basal and cauline leaves.*—Long and narrowly apicultate.

*Base, basal and cauline leaves.*—Cordate to hastate; when hastate, lobes are touching to slightly imbricate.

*Margin, basal and cauline leaves.*—Entire; undulate.

*Texture and luster, basal and cauline leaves, upper and lower surfaces.*—Moderately pubescent; matte.

*Venation pattern, basal and cauline leaves.*—Pinnate; veins furrowed.

*Color, basal and cauline leaves.*—Developing leaves, upper surface: Close to 137A. Developing leaves, lower surface: Close to between 138A and 138B. Fully expanded leaves, upper surface: Close to 137B; venation, close to 148B to 148C. Fully expanded leaves, lower surface: Close to between 138A and 147B; venation, close to 150D.

*Petioles.*—Length, basal leaves: About 3.7 cm. Diameter, basal leaves: About 5 mm. Length, cauline leaves: About 5.6 cm. Diameter, cauline leaves: About 3 mm. Strength, basal and cauline leaves: Strong. Texture and luster, basal and cauline leaves, upper surface: Moderately pubescent; moderately glossy. Texture and luster, basal and cauline leaves, lower surface: Smooth, glabrous; moderately glossy. Color, basal leaves: Upper surface: Close to 146C to 146D, slightly to strongly tined with close to 165B. Lower surface: Close to 146C. Color, cauline leaves: Upper surface: Close to 144A, slightly to strongly tined with close to 165B. Lower surface: Close to 144B.

*Stipules*.—Quantity and appearance: One leafy stipule at the base of each leaf. Length: About 5.8 cm. Width: About 1.1 cm. Shape: Lanceolate. Apex: Narrowly acuminate. Base: Broadly cuneate. Margin: Entire. Texture and luster: Smooth, glabrous; slightly glossy. Color: Developing stipules, upper and lower surfaces: Close to 145D and towards the apex, close to 165C. Fully developed stipules, upper and lower surfaces: Close to between 165B and N199D and towards the base, close to 145C.

Flower description:

*Flower arrangement and shape*.—Single rotate flowers arranged on long slender and straight racemes; freely flowering habit with about 200 flowers developing per inflorescence and more than 20,000 flowers developing per plant during the flowering season; flowers face mostly outwardly to slightly upright.

*Fragrance*.—None detected.

*Natural flowering season*.—Plants begin flowering about ten months after planting; plants flower naturally from July to Lte September in an outdoor environment in The Netherlands; flowers last about one week on the plant, flowers not persistent.

*Flower buds*.—Length: About 4 mm. Diameter: About 1.75 mm. Shape: Ovate. Texture and luster: Smooth, glabrous; matte. Color: Close to between 58B to 58C.

*Inflorescence height*.—About 12.6 cm.

*Inflorescence diameter*.—About 1.5 cm.

*Flower size*.—About 8 mm by 8 mm.

*Flower depth*.—About 4 mm.

*Tepals*.—Quantity and arrangement: Five tepals arranged in a single whorl. Length: About 4 mm. Width: About 2 mm. Shape: Ovate, flat to very slightly concave. Apex: Obtuse. Base: Cuneate. Margin: Entire; not undulate. Texture and luster, upper and lower surfaces: Smooth, glabrous; slightly velvety; pubescent; matte. Color: When opening, upper and lower surfaces: Close to 58C. Fully opened, upper surface: Close to between 58C and 58D; venation, close to between 58C to 58D; color becoming closer to slightly lighter than 58D with development. Fully opened, lower surface: Close to between 58C and 58D; venation, close to slightly lighter than 58D; color becoming closer to slightly lighter than 58D with development.

*Peduncles*.—Length: About 22.7 cm. Diameter: About 1.75 mm. Strength: Strong. Aspect: Mostly erect. Texture and luster: Smooth, glabrous; moderately glossy. Color: Close to 144A; sun-exposed surfaces, tinged with close to 178A.

*Pedicels*.—Length: About 6 mm. Diameter: About 0.5 mm. Strength: Moderately strong. Aspect: About 30° from peduncle axis. Texture and luster: Smooth, glabrous; matte. Color: Close to 52B.

*Floral bracts*.—Quantity and appearance: One floral bract at the base of a cluster of three flowers. Length: About 6 mm. Width: About 2.5 mm. Shape: Ovate. Apex: Apiculate. Base: Cuneate. Margin: Entire. Texture and luster: Smooth, glabrous; matte. Color, upper and lower surfaces: Close to 200D; towards the margins, close to 199C.

*Reproductive organs*.—Stamens: Quantity per flower: Typically six to eight. Filament length: About 2 mm. Filament color: Close to 58C; proximal end, close to 58D. Anther shape: Broadly ovate; basifixed. Anther size: About 0.5 mm by 0.75 mm. Anther color: Close to 79A to 79B. Pollen amount: Scarce. Pollen color: Close to 202C. Pistils: Quantity per flower: Three. Pistil length: About 2 mm. Stigma diameter: About 0.2 mm. Stigma shape: Pointed. Stigma color: Close to 58B to 58C. Style length: Less than 2 mm. Style color: Close to 58B to 58C. Ovary color: Close to 144B.

*Seeds and fruits*.—To date, seed and fruit production has not been observed on plants of the new *Persicaria*.

Pathogen & pest resistance: To date, plants of the new *Persicaria* have not been noted to be resistant to pathogens and pests common to *Persicaria* plants.

Garden performance: Plants of the new *Persicaria* have exhibited good garden performance, to tolerate temperatures ranging from −23° C. to about 40° C. and to be suitable for USDA Hardiness Zones 5 to 10.

It is claimed:

1. A new and distinct *Persicaria* plant named 'Flamingo Feathers' as illustrated and described.

* * * * *